US00PP34886P2

(12) United States Plant Patent
Ciccolella

(10) Patent No.: US PP34,886 P2
(45) Date of Patent: Jan. 3, 2023

(54) ***ABELIA* PLANT NAMED 'PINK'**

(50) Latin Name: *Abelia grandiflora nana*
Varietal Denomination: Pink

(71) Applicant: Vic Ciccolella, Oakville (AU)

(72) Inventor: Vic Ciccolella, Oakville (AU)

( * ) Notice: Subject to any disclaimer, the term of this patent is extended or adjusted under 35 U.S.C. 154(b) by 0 days.

(21) Appl. No.: 17/893,701

(22) Filed: Aug. 23, 2022

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Abelia* named 'Pink' which exhibits a compact upright plant habit in its first year of growth and a dense mounding and spreading plant habit in its second and subsequent years of growth. The stems of 'Pink' are mid-red to dark-red in color. The foliage of 'Pink' is variegated, with green centers and narrow pink marginal bands, the pink color of which intensifies through the season, changing from white or pale pink in winter and early spring, to deep pink by mid-summer. The flower buds of 'Pink' are white and mauve-pink in color and the flowers of 'Pink' become pure white in color when fully expanded. In combination, these characteristics. In combination, these traits distinguish 'Pink' from all other varieties of *Abelia* known to the inventor.

2 Drawing Sheets

Genus and species: *Abelia grandiflora nana.*
Variety denomination: 'Pink'.

BACKGROUND

The present disclosure relates to a new and distinct cultivar of *Abelia* plant, a shrub that is grown for use as an ornamental landscape and container plant. The new variety is known botanically as *Abelia grandiflora nana* and will be referred to hereinafter by the cultivar name 'Pink'.

'Pink' was first observed by the inventor as a naturally occurring variegated branch sport which was growing on a single plant of non-variegated *Abelia grandiflora* (species, unnamed, unpatented) in the inventor's nursery in Oakville, New South Wales, Australia. *Abelia grandiflora nana* is a shrub grown for its non-variegated glossy green foliage. In 2011, the inventor observed that one of his plants of *Abelia grandiflora nana* had developed a stem which bore pink-edged variegated foliage along its length. In 2012, the inventor took and rooted a small number of softwood cuttings in order to establish the variegated form on its own roots, to evaluate its stability, and to increase numbers for commercial introduction.

The inventor has determined that 'Pink' is a stable cultivar which reproduces true-to-type in successive generations of asexual reproduction.

SUMMARY

The following traits have been repeatedly observed and represent the distinguishing characteristics of 'Pink'. 'Pink' has not been tested under all possible conditions and phenotypic differences may be observed with variations in environmental, climatic, and cultural conditions, without however, any variance in genotype.

1. 'Pink' exhibits a compact upright plant habit in its first year of growth and a dense mounding and spreading plant habit in its second and subsequent years of growth.
2. The stems of 'Pink' are mid-red to dark-red in color.
3. The foliage of 'Pink' is variegated, with green centers and narrow pink marginal bands.
4. The pink coloration of the leaf marginal bands intensifies through the season, changing from white or pale pink in winter and early spring, to deep pink by mid-summer.
5. The pink coloration of the leaf marginal bands is intensified when plants of 'Pink' are exposed to full sun.
6. The foliage of 'Pink' does not burn or bleach in full sun.
7. The flower buds of 'Pink' are white and mauve-pink in color.
8. The flowers of 'Pink' become pure white in color when fully expanded.

DESCRIPTION OF THE PHOTOGRAPHS

The accompanying color photographs illustrate the overall appearance of the new *Abelia* cultivar 'Pink' showing the colors as true as it is reasonably possible to obtain in colored reproductions of this type. Photographs were taken in August 2022 in Santa Barbara, Calif. from a two-year-old plant grown outdoors in a 3-gallon container, with one pinch after initial cutting establishment and without any chemical growth regulators. Plants of 'Pink' have developed their characteristic pink-colored leaf margins at this time of year. Colors in the photographs may differ from the color values cited in the detailed botanical description, which accurately describes the actual colors of the new variety 'Pink'.

DESCRIPTION OF THE NEW VARIETY

Figure 1:
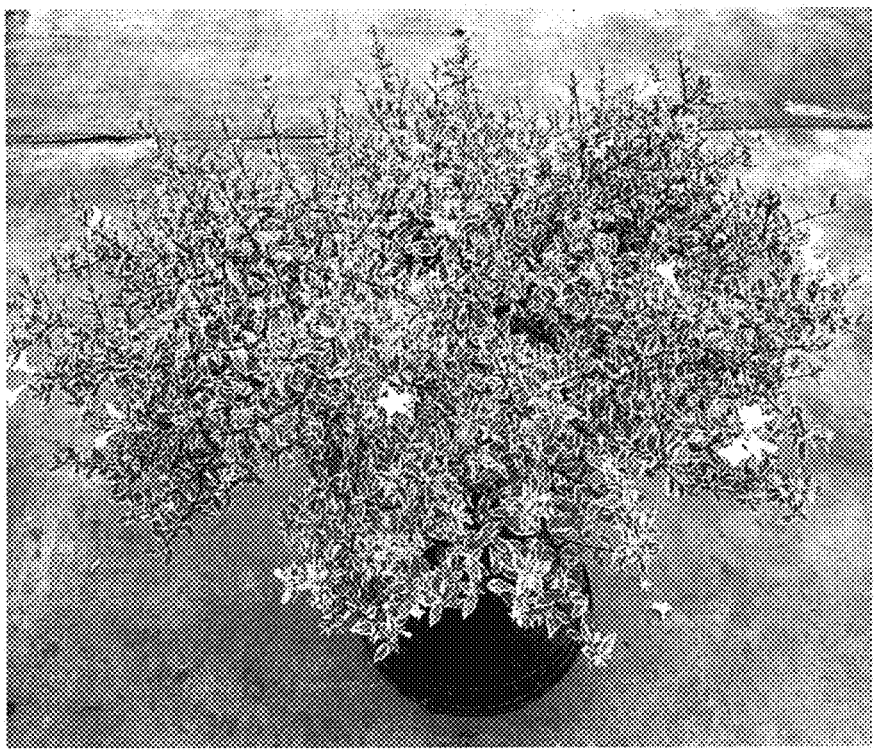
FIG. 1 depicts an entire plant of 'Pink' in flower in August.
Figure 2:
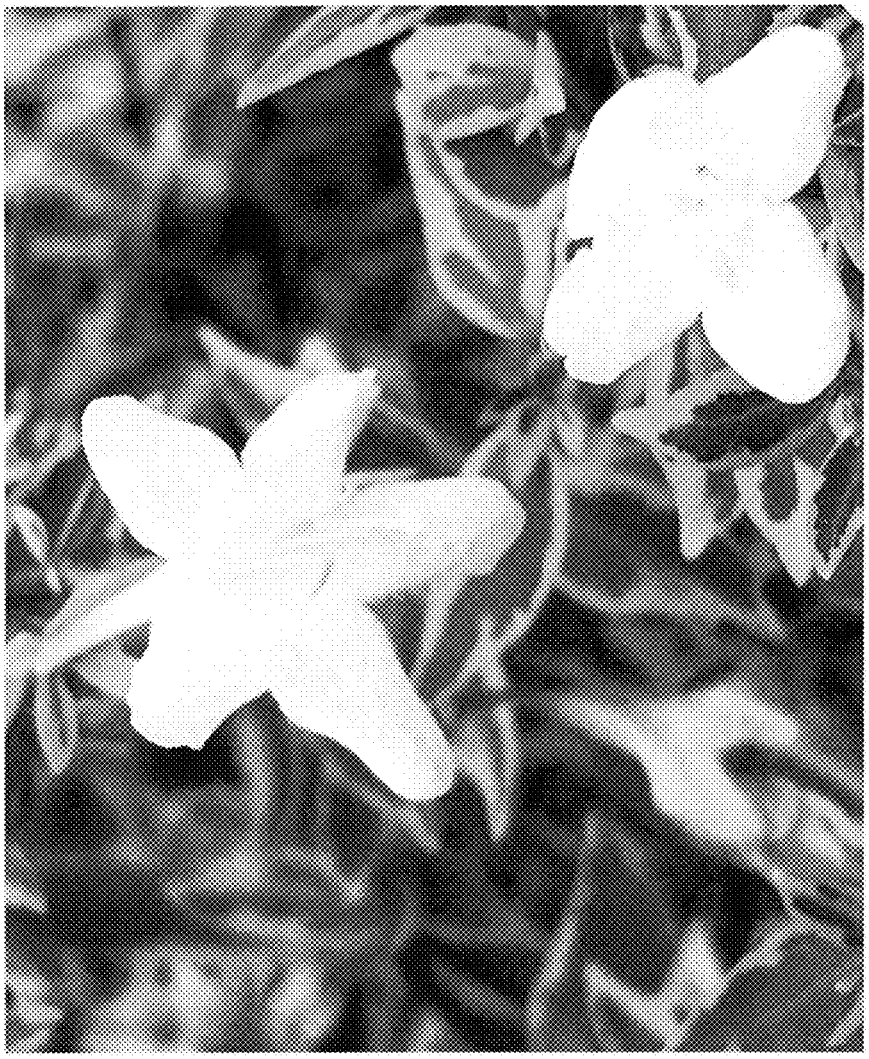
FIG. 2 depicts a close-up view of the foliage and flowers of 'Pink' in August.

The following detailed descriptions set forth the distinctive characteristics of 'Pink'. Observations, measurements, values, and comparisons were collected in August 2022 in Santa Barbara, Calif. from five months old plants growing in a 1 quart container. The plants were growing outdoors in full sun with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Caprifoliaceae.

*Genus*.—*Abelia*.

*Species*.—*grandiflora nana*.

Parentage: Naturally occurring branch sport found on one unnamed, unpatented plant of the species *Abelia grandiflora nana*.

Plant:

*Propagation method*.—Softwood tip cuttings.

*Rooting system*.—Fine and fibrous, root color NN155D.

*Vigor*.—Moderate vigor.

*Time to develop roots*.—7-10 days are needed for a cutting to develop roots at recommended rooting temperature of 20° to 22° Centigrade.

*Crop time* (*1-quart container*).—Approximately 5 months.

*Crop time* (*2-gallon container*).—Approximately 2 years.

*Suggested container size*.—Quart to two-gallon container.

*Use*.—Ornamental shrub which is colorful year-round in the landscape or in planted containers.

*Type, hardiness*.—Evergreen in USDA Hardiness Zones 7 and above. Semi-deciduous in Zone 6.

*Dimensions* (*5 months old plant in 1-quart container*).—16 cm in height, and 20 cm in width.

*Dimensions* (*2 years old plant in a 2-gallon container*).—25-30 cm in height, 35-40 cm in width.

*Cultural requirements*.—Propagate cuttings and grow young plants in semi-shade.

*Established plants may be grown in full sun with moderate water and well-draining soil.*

*Form*.—Compact upright in first year of growth, mounding and spreading in second and subsequent years.

*Blooming season*.—From early summer to fall.

Stems (below first pinch):

*Condition*.—Lignified.

*Shape*.—Terete.

*Length*.—1 cm.

*Diameter*.—4 mm.

*Bark description*.—Papery and slightly peeling.

*Bark color*.—198A and 197A both present.

*Texture*.—Rough.

Branches:

*Quantity*.—4-6 are primary branches and 30 or more lateral branches.

*Shape*.—Terete.

*Primary branch dimensions*.—15 cm in length, 3 mm in diameter at base, 1.5 mm in diameter towards apex.

*Lateral branch dimensions*.—4-12 cm in length, 1.5 mm in diameter.

*Internode length* (*all branches*).—7 mm-15 mm.

*Branch color, surface* (*older growth of primary branches*).—198A and 197A, rough.

*Branch color* (*new growth of primary branches, all growth of lateral branches*).—Ranging between 59A towards base and 46A towards apex (newest growth), smooth, glabrous, semi-glossy.

Leaves:

*Type*.—Simple.

*Variegation*.—All leaves bicolored with green centers and narrow marginal bands ranging in color from white to deep pink.

*Arrangement*.—Opposite pairs.

*Attachment*.—Short petiolate.

*Quantity per branch*.—6 to 8 pairs.

*Shape*.—Lanceolate.

*Length*.—Up to 35 mm.

*Width*.—Up to 15 mm.

*Apex*.—Acute.

*Base*.—Rounded.

*Margin*.—Smooth, entire.

*Leaf marginal band width* (*both surfaces*).—Predominantly between 0.5 mm and 1.5 mm, occasionally up to 2.5 mm.

*Leaf colors* (*older leaves in combination with white or pale pink marginal bands*).—Center color, adaxial surface: 137B. Center color, abaxial surface: 138B. Margin band color (both surfaces): Ranges between NN155B and 55D.

*Leaf colors* (*young developing foliage in combination with pink or dark pink marginal bands*).—Center color, adaxial surface: N137B. Center color, abaxial surface: 138B. Margin band color (both surfaces): Ranges between 55C and 54A.

*Venation*.—Pinnate, veins fine and barely visible except raised midrib on abaxial surface.

*Vein colors* (*both surfaces*).—As adjacent leaf lamina except abaxial midrib 145C.

*Leaf texture* (*both surfaces*).—Smooth, glabrous, glossy.

*Fragrance*.—None.

Petiole:

*Shape*.—Sulcate.

*Length*.—2 mm.

*Width*.—1.0 mm.

*Texture*.—Smooth, glabrous.

*Color*.—As marginal band, ranging between NN155B and 54A.

Inflorescence:

*Type*.—Cyme, flowers borne singly on short peduncles in branch terminal leaf axils.

*Flowers*.—Funnelform, five-petals fused to form corolla tube, then free to form flared petal apices.

*Quantity of flowers per branch* (*buds and flowers*).—6-8.

*Quantity of flowers per plant* (*buds and flowers*).—Approximately 60.

*Flower depth* (*including corolla tube*).—23 mm.
*Flower diameter* (*across petal apices, fully expanded*).—18 mm.
*Flower aspect*.—Outward facing, horizontal or upright.
*Fragrance*.—Light sweet perfume.
*Lastingness and persistence of flowers*.—Once fully open, flowers discolor after 2-3 days and fall away after 5-6 days.

Peduncle:
*Length*.—5 mm.
*Shape*.—Terete, slightly swollen at mid-length.
*Diameter*.—1.5 mm-2.0 mm.
*Texture*.—Smooth, lightly puberulent.
*Color*.—151A towards attachment, 182D below calyx.

Calyx:
*Shape*.—Stellate.
*Height*.—4 mm.
*Diameter across sepal apices*.—8 mm.

Sepals:
*Quantity*.—5, basally fused.
*Length*.—7 mm.
*Width*.—2.5 mm.
*Shape*.—Narrow lanceolate.
*Apex*.—Acute.
*Base*.—Truncate.
*Margin*.—Entire.
*Texture* (*both surfaces*).—Glabrous.
*Color* (*both surfaces*).—54B.

Bud (prior to opening):
*Shape*.—Club-shaped.
*Color*.—Initially NN155A with mauve pink 75C to 70B on upper surfaces of bud apex, becoming white NN155A throughout.
*Bud surface*.—Faintly puberulent.
*Bud dimensions*.—15 mm. in length and 4 mm-5 mm. in diameter.

Corolla:
*Corolla tube dimensions* (*to base of free petal lobes*).—17 mm. in length, 2-3 mm in diameter at base, 7 mm in diameter at base of petal lobes.
*Corolla tube surface* (*inner surface*).—Lightly puberulent.
*Corolla tube surface* (*outer surface*).—Glabrous.
*Corolla tube color* (*inner surface*).—N155D.
*Corolla tube color* (*outer surface*).—NN155D.

Petals:
*Petals*.—Five in number, basally fused, free orbicular lobes.
*Petal lobe aspect*.—Outward and upward, becoming recurved with age.
*Petal length*.—23 mm, of which 17 mm fused to form corolla tube, 6 mm free petal lobes.
*Petal lobe dimensions*.—6 mm in length, 4 mm in width.
*Petal lobe surface* (*adaxial surface*).—Pubescent, hairs fine, color NN155D.
*Petal surface* (*abaxial surface*).—Glabrous.
*Petal color* (*both surfaces*).—Initially NN155D or NN155D with shades of mauve-pink 75D, becoming pure white NN155D when fully expanded.
*Petal apex*.—Rounded.
*Petal base*.—Truncate.
*Petal margins*.—Entire.

Reproductive organs:
*Stamens*.—Quantity: 4. Filaments: Free, length 13 mm, diameter 0.5 mm. Color: NN155D.
*Anthers*.—Shape: Ellipsoid, basally attached. Dimensions: 1.5 mm in length, 0.5 mm in width. Color: 158C to 158D.
*Pollen*.—None.
*Pistil*.—Quantity: 1. Style: 14 mm in length, 0.5 mm in diameter.
*Stigma*.—Position: Held approximately 1 mm above anthers. Shape, dimensions: Flattened globe, 0.5 mm in height, 1 mm in diameter. Color: NN155B.
*Ovary*.—Not observed.

Seed: None

Disease and pest susceptibility: Susceptible to aphids (*aphis gossypii*) when stressed. Generally outgrows most bacterial diseases.

Heat, humidity and drought tolerance: Very tolerant of full sun and high humidity when established in the landscape or planted in well-watered containers. Moderate drought tolerance.

COMPARISON WITH PARENTAL LINES AND KNOWN VARIETY

In comparison with the parent, 'Pink' exhibits variegated foliage. The unnamed, unpatented parent plant bears green non-variegated foliage.

The closest variety of variegated *Abelia* known to the inventor is *Abelia* Plant Named 'Kaleidoscope' (U.S. Plant Pat. No. 16,988). Whereas the color of the foliage of 'Kaleidoscope' ranges through green, golden yellow, to bright scarlet-red in summer and fall, the color of the foliage of 'Pink' is green with narrow pink marginal bands.

I claim:

1. A new and distinct cultivar of *Abelia* plant named 'Pink' as described and illustrated herein.

* * * * *